United States Patent [19]
Holmes et al.

[11] Patent Number: 4,880,000
[45] Date of Patent: Nov. 14, 1989

[54] LENS INSERTION INSTRUMENT

[75] Inventors: Martin J. Holmes, Los Angeles; Ron Harris, Claremont, both of Calif.

[73] Assignee: Iolab Corporation, Claremont, Calif.

[21] Appl. No.: 132,290

[22] Filed: Dec. 15, 1987

[51] Int. Cl.$^4$ ............................................. A61F 2/16
[52] U.S. Cl. ................................... 128/303 R; 623/6
[58] Field of Search ................... 128/303 R, 321, 354, 128/1 R; 604/57, 59, 60, 104, 106, 107, 164, 170; 623/6

[56] References Cited

U.S. PATENT DOCUMENTS

| | | | |
|---|---|---|---|
| 3,132,887 | 5/1964 | Martinez | 128/303 R |
| 4,198,980 | 4/1980 | Clark | 128/303 R |
| 4,325,375 | 4/1982 | Neuyas | 128/321 |
| 4,573,998 | 3/1986 | Mazzocco | 623/6 |
| 4,600,003 | 7/1986 | Lopez | 128/303 R |
| 4,607,617 | 8/1986 | Choyce | 128/305 |
| 4,642,090 | 2/1987 | Utrata | 128/305 |
| 4,674,500 | 6/1987 | De Satnick | 128/305 |
| 4,681,102 | 7/1987 | Bartell | 623/6 |
| 4,711,638 | 12/1987 | Lindstrom | 128/303 R |
| 4,715,373 | 12/1987 | Mazzocco et al. | 128/321 |
| 4,750,498 | 6/1988 | Graham | 128/303 R |
| 4,759,359 | 7/1988 | Willis et al. | 128/303 R |
| 4,763,650 | 8/1988 | Hauser | 128/303 R |
| 4,765,329 | 8/1988 | Cumming et al. | 128/303 R |
| 4,781,719 | 11/1988 | Kelman | 128/303 R |
| 4,787,904 | 11/1988 | Severin et al. | 128/303 R |

Primary Examiner—Stephen C. Pellegrino
Assistant Examiner—Ralph Lewis
Attorney, Agent, or Firm—Donal B. Tobin

[57] ABSTRACT

An insertion tool for an intraocular lens including a hollow barrel, a rigid annular tube extending from the distal end of the barrel, the stylet for reciprocating within the barrel and the rigid tube, an actuator extending through the side wall of the barrel and connected to the stylet to permit the user to move the stylet back and forth within the barrel. A paddle is attached to the distal end of the stylet. The intraocular lens is loaded into the paddle and then the paddle and the lens are retracted into the rigid tube for insertion into the eye through a small incision. The paddle unfolds the lens as it is retracted into the tube. When the distal end of the instrument is placed into the eye, the paddle and lens are ejected from the tube so that the lens may be deposited within the eye.

12 Claims, 5 Drawing Sheets

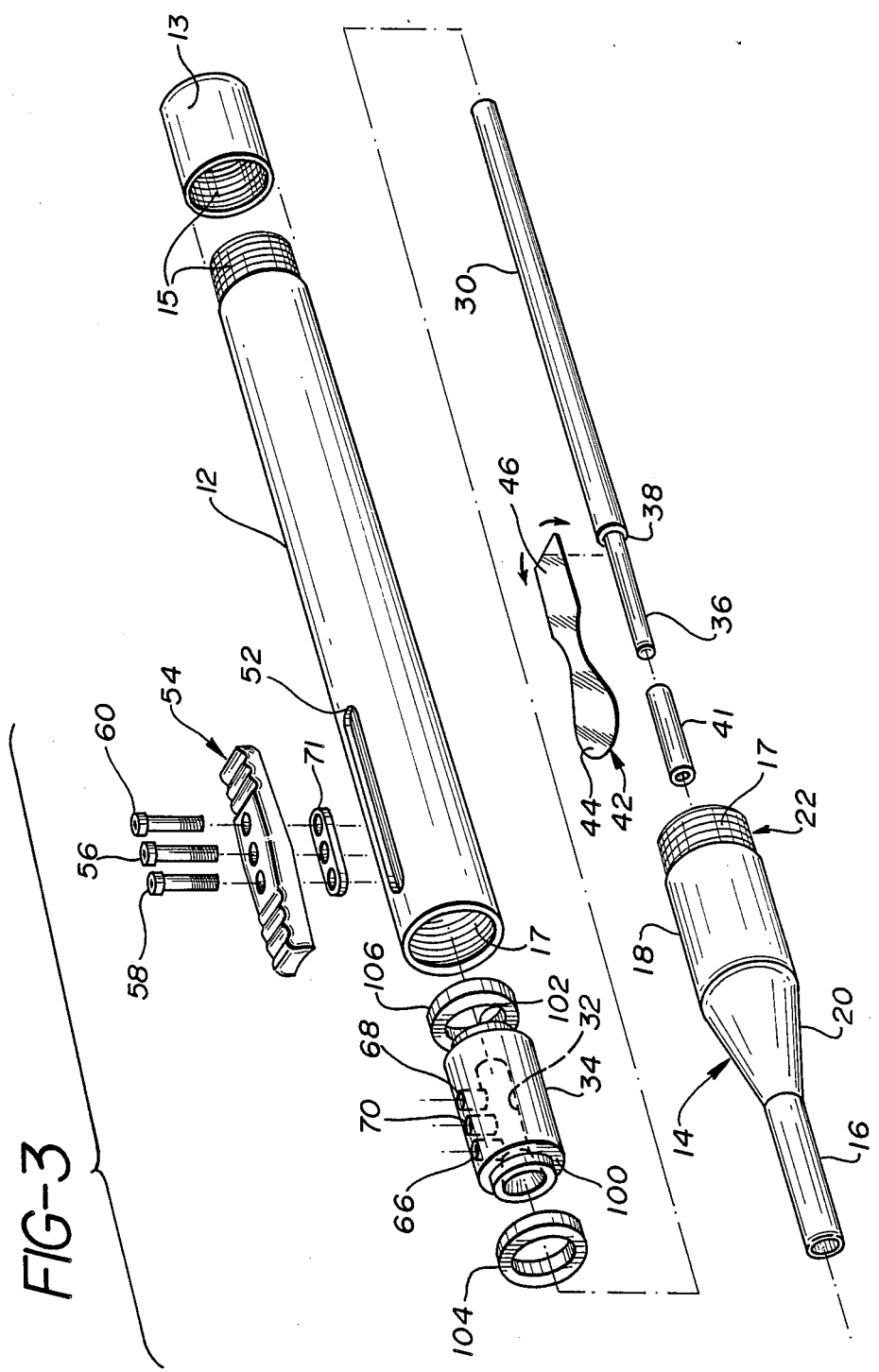

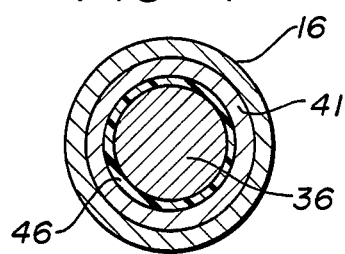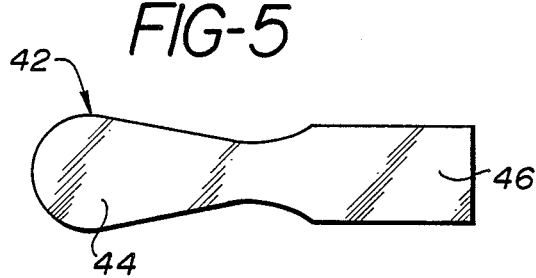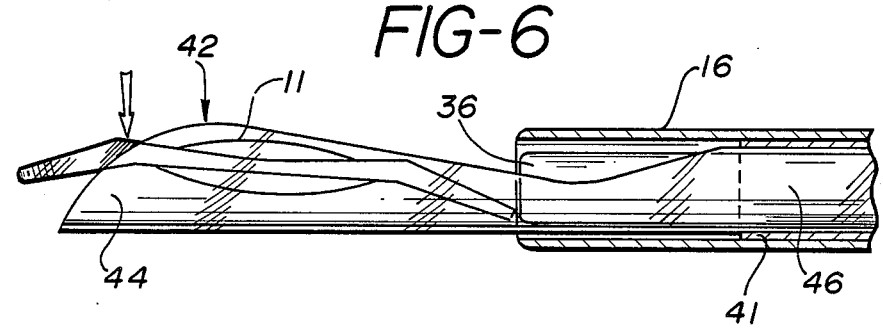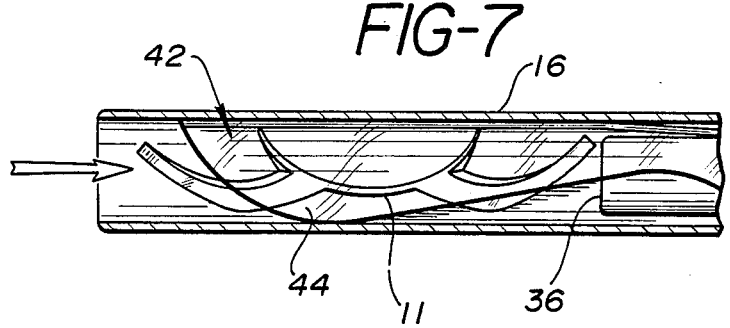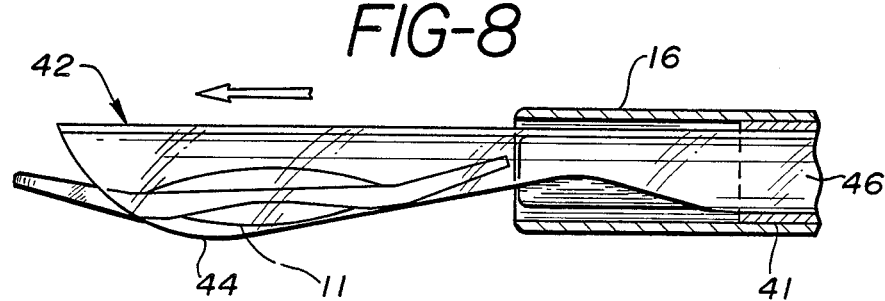

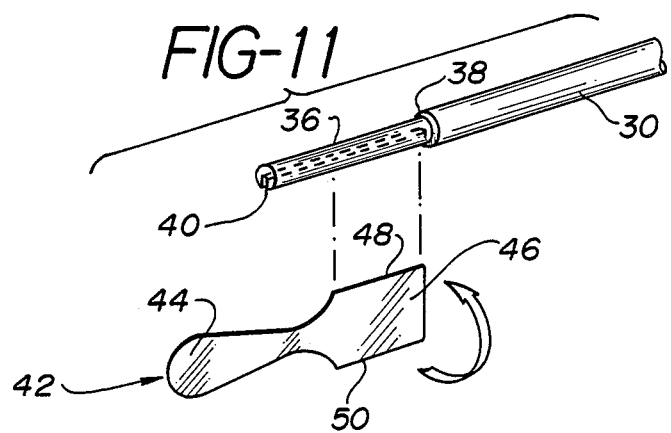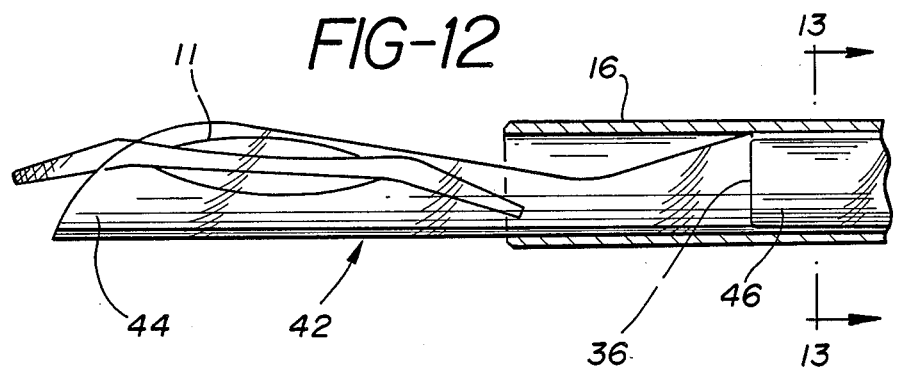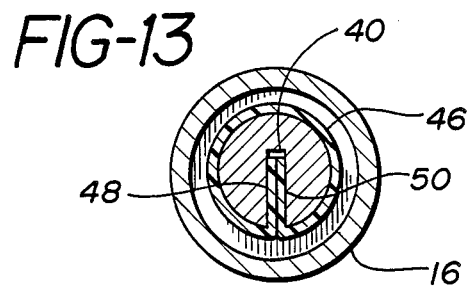

LENS INSERTION INSTRUMENT

FIELD OF THE INVENTION

The present invention relates to a surgical instrument for inserting an intraocular lens into the eye and, more particularly, for inserting a soft foldable intraocular lens through a small incision.

BACKGROUND OF THE INVENTION

When one develops the condition of cataracts, the usually clear natural lens of the eye becomes partially or completely opaque so that the passage of light to the retina is partially or totally inhibited. The problems of cataracts can be substantially alleviated by removing the cataract lens and replacing it with a man-made implant.

There is a large variety of possible intraocular lens implants available for use in cataract surgery. There is also a variety of methods for inserting the lens into the eye. Many medical practitioners have expressed a desire to have a tool which would hold the lens during insertion and permit the lens to be inserted through a small incision. A small incision is an incision smaller than the minimum dimension of the outer envelope of the lens when it is in a completely relaxed condition.

Certain intraocular lenses are made of flexible materials like silicone or hydrogel. Such lenses may be folded into a very small shape and inserted through a very small incision. Once the lens is inside the eye it is possible to have the lens relax and expand to its original shape. Certain medical practitioners believe that the smaller the incision through which the intraocular lens implant is introduced into the eye the better. Smaller incisions are believed to create less trauma for the patient with fewer sutures required and allow the healing process to proceed more quickly. Many procedures which use relatively large incisions, which are larger than the minimum dimension of the envelope of the lens, have been used for many years with satisfactory results. Some believe the smaller incision to provide further and additional benefits, but this is not to suggest that the use of a larger incision is in any way unsatisfactory.

In order to insert a lens through a small incision, it is necessary to reduce the size of the envelope of the lens. It would be convenient to have a tool which can readily reduce the size of the lens for insertion through a small incision and then easily release the lens once it is inside the eye.

It would also be desirable to have a reusable portion on the lens insertion tool which could be sterilized and used on a variety of patients and a disposable portion which would come in contact with the lens and with the eye of the patient.

Throughout this application the word distal is used to describe that portion of the instrument which extends away from the user during use whereas the word proximal is used to describe that portion of the instrument that extends toward the user during use.

Throughout this application the word cylindrical is used to describe the shape of various parts. The word cylindrical is not meant to be limited to a right circular cylinder but can include any shape which can be generated by moving a line parallel to itself about an axis and could include a circular, oval, square, rectangular or a polyhedronal cross section.

SUMMARY OF THE INVENTION

The present invention provides a surgical instrument for facilitating the insertion of an intraocular lens into the eye. The instrument includes a stylet and paddle attached to the distal end of the stylet. The stylet may be affixed to the paddle by means of a slot extending transversely into the exterior surface of the stylet near its distal end. Alternatively, the paddle may be attached to the stylet using an annular sleeve over the outside of a portion of the paddle and stylet.

The paddle can include a lens-holding portion and a mounting portion. In one embodiment, the mounting portion includes margins to wrap around the distal portion of the stylet and fit into the slot. There may be a recess on the distal end of the stylet to accomodate the paddle and the annular sleeve, if used, so that the assembled paddle and stylet have a smooth exterior surface.

The stylet may be mounted into a piston which can reciprocate within a hollow barrel. A slot in the side of the barrel provides access for an actuation mechanism which connects to the piston and can be operated by a user. Bushings can be provided on the piston to fascilitate easy motion.

A rigid tube can be connected to the distal end of the hollow barrel and preferably includes a tubular distal section, a mounting base and a conic transition section between the tubular distal section and the mounting base. The stylet is intended to reciprocate within the rigid tube.

When the stylet is moved distally, the lens-holder portion of the paddle is ejected from the rigid tube and a lens is placed in the lens holder. The stylet is then retracted within the rigid tube and the paddle folds around the lens as the lens and the paddle are compressed during retraction into the rigid tube. When the paddle is ejected from the rigid tube, the paddle extends in a direction transverse to the axis of the stylet a distance greater than the largest transverse dimension of the rigid tube.

The paddle is preferably made of of a thin, flexible film and is adapted to fold to a generally closed position as it is retracted into the rigid tube to hold, and at least partially surround, the intraocular lens. The paddle is preferably disposable.

The hollow barrel may have an opening in its proximal end to permit air to escape from the hollow barrel so that air trapped within the hollow barrel does not impede the smooth motion of the stylet.

There may be a stop on the acuation mechanism to interact with the slot in the side wall of the barrel to control the distance which the stylet reciprocates within the barrel.

BRIEF DESCRIPTION OF THE DRAWINGS

These and other features of the present invention will become apparent from the following description of certain embodiments of the invention taken in conjunction with the following drawings.

FIG. 3 shows a exploded perspective view of the instrument of FIG. 1;

FIG. 4 shows a cross-sectional view of the instrument taken along line 4—4 in FIG. 2;

FIG. 5 shows a plan view of the paddle portion of the present invention;

FIG. 6 shows a side elevation, partly in section, of the distal end of the instrument of FIG. 1, but rolled over 180° so that the lens may be placed within the paddle;

FIG. 7 shows a side elevation, partly in section, of the distal end of the instrument in FIG. 1 in the same orientation as FIG. 1 with the lens retracted within the instrument;

FIG. 8 shows a side elevation, partly in section, of the distal end of the instrument of FIG. 1 in the same orientation as FIG. 1 with the lens being ejected from the instrument;

FIG. 11 is a sectional view of the distal end of an alternative embodiment of the instrument;

FIG. 12 shows a side elevational view, partly in section of the embodiment of FIG. 11; and, FIG. 13 is a cross sectional view taken along lines 13—13 in FIG. 12.

DETAILED DESCRIPTION OF THE PREFERRED EMBODIMENT

Figure 1:
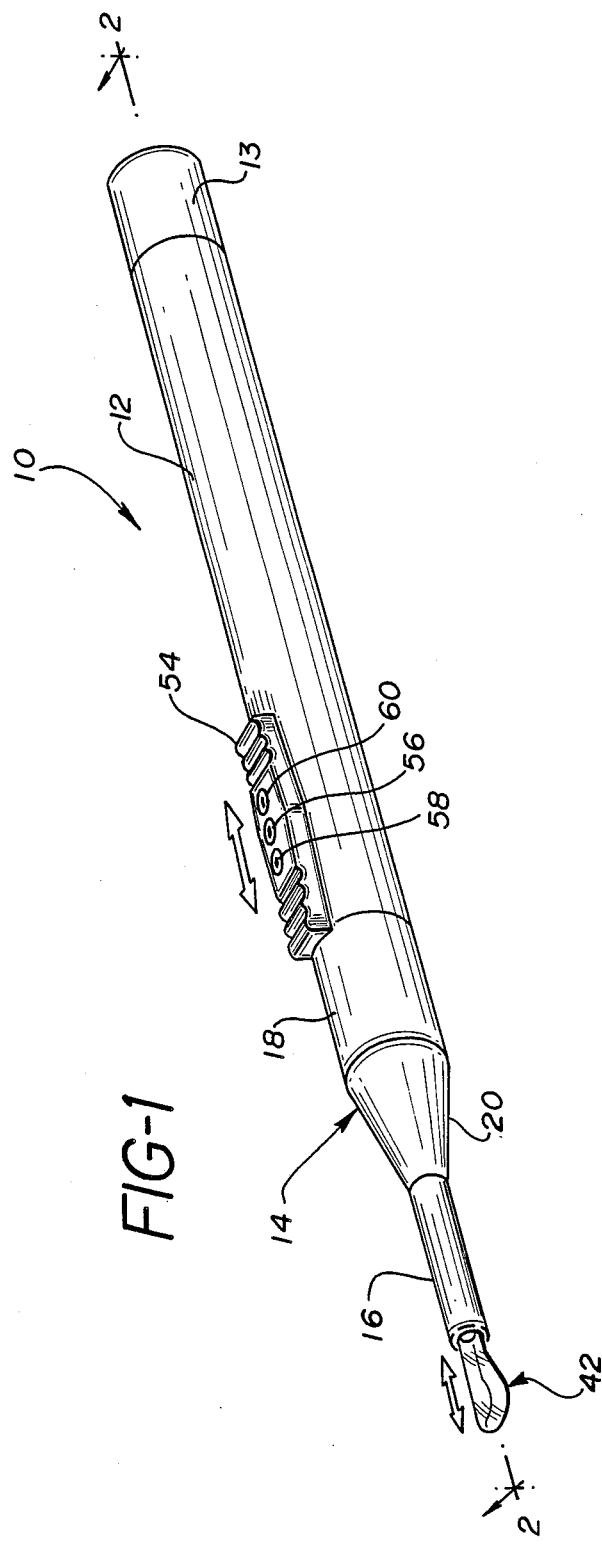
FIG. 1 shows a perspective view of the instrument.

Referring now to FIG. 1, there shown a surgical instrument 10 of the present invention including a hollow barrel 12 which is preferably a reusable piece made of stainless steel or some other durable, sterilizable material. A rigid tube 14 preferably made of stainless steel or some other durable, sterilizable material or alternatively made of a disposable plastic material extends distally from the distal end of barrel 12. Rigid tube 14 is hollow and has a tubular distal section 16, a cylindrical mounting base 18 and a transition section 20 which is preferably conic to provide a smooth transition between tubular distal section 16 and mounting base 18.

Figure 2:
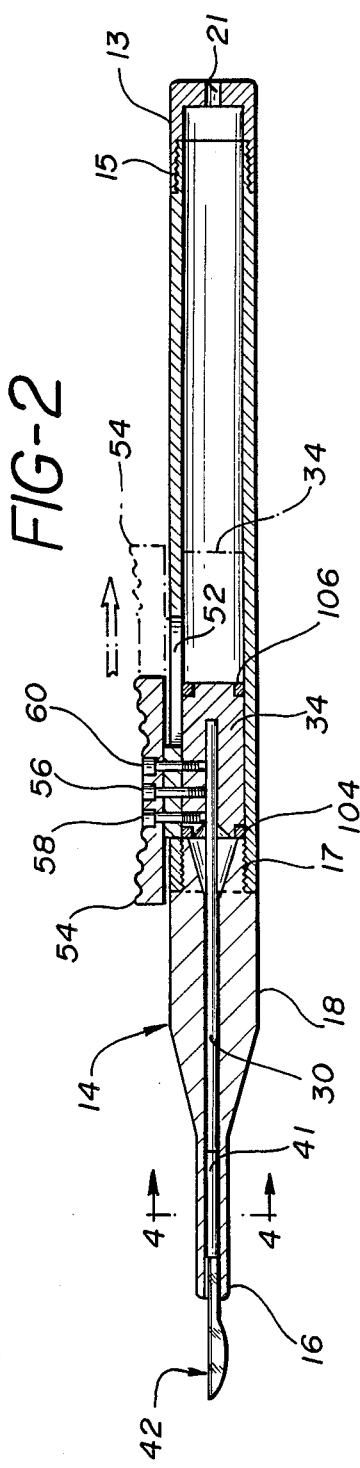
FIG. 2 shows a cross-sectional view of the instrument of FIG. 1 taken along line 2—2 in FIG. 1.
Figure 9:
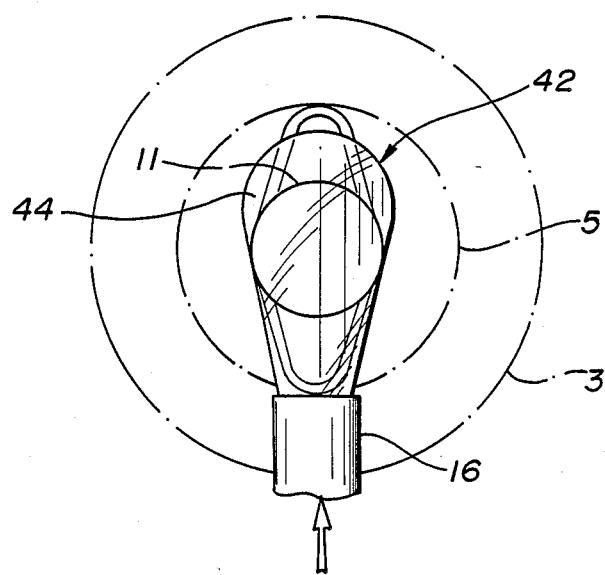
FIG. 9 shows a schematic plan view of the anatomy of the eye with the instrument being used to insert the lens.

Referring now to FIG. 2, the proximal portion of mounting base 18 includes a projection or skirt 22 for attaching mounting base 18 to hollow barrel 12. Hollow barrel 12 has an air escape hole 21 in its proximal end. Hollow barrel 12 preferably has a separate end cap 13 which contains air escape hole 21 and which attaches to the proximal end of barrel 12 by press fit or by cooperating threads 15 on barrel 12 and end cap 13.

The confronting surfaces of skirt 22 and the interior distal surface of barrel 12 may be provided with cooperative threads 17 to attach mounting base 18 to barrel 12. Alternatively, a variety of suitable connection means, i.e., a tight fit can be used to connect these two parts together.

Still referring to FIG. 2, there is shown a stylet 30 mounted within bore 32 of piston 34. Stylet 30 is preferably made of a durable, sterilizable and reusable material like stainless steel or, alternatively, may be made of plastic. Piston 34 is preferably made of a durable, sterilizable, reusable material such as stainless steel.

Referring now particularly to FIGS. 3, 4 and 5, it can be seen that the distal end 36 of stylet 30 includes a recess 38. A stainless steel reusable sleeve 41 which fits over distal end 36 of stylet 30 and over paddle 22 to hold paddle 22 in place. Alternatively sleeve 41 may be eliminated and replaced by an axially-extending slot 40 projecting into the side wall of stylet 30 in the vicinity of distal end 36.

Paddle 42 is preferably made of very thin, flexible transparent plastic like acetate. Any suitable material may be used. In the alternative embodiment of FIGS. 11–13, paddle 42 has a holding portion 44 and a base portion 46. Base portion 46 has two margins 48 and 50 which slide into slot 40 at the distal end of stylet 30 to hold mounting portion 46 on the distal end of stylet 30. If sleeve 41 is used (see FIG. 3) margins 48 and 50 may be eliminated. Paddle 42 may also be suitably attached to the distal portion 36 of stylet 30 by means of a suitable adhesive. Holding portion 44 of paddle 42 projects beyond the distal end of stylet 30 as shown in FIGS. 2 and 6. As will be explained later in the application, holding portion 44 holds an intraocular lens 11 for insertion into the eye. As seen in FIGS. 2 and 3, the thickness of mounting portion 46 of paddle 42 is approximately equal to the depth of recess 38 at distal end 36 of stylet 30 so that when paddle 42 is mounted on the distal end 36 of stylet 30, there is a smooth transition between the outer surface of mounting portion 46 and the outer surface of stylet 30.

If sleeve 41 is used the thickness of sleeve 41, paddle 42 and recess 38 are chosen to provide a smooth transition on the outer surface of stylet 30.

Referring again to FIGS. 2 and 3, it can be seen that hollow barrel 12 has a slot 52 extending through its side wall to permit access to the inside of hollow barrel 12. Actuator 54 slides along the surface of hollow barrel 12 and connects by means of screw 56 to piston 34 to provide a means for driving piston 34 and stylet 30 back and forth within hollow barrel 12 and for holding stylet 30 within piston 34. Actuator 54 and screw 56 are made of durable, reusable material like stainless steel, and screw 56 is counter-sunk in actuator 54. Additional screws 58 and 60 fit into threaded bores 66 and 68 in piston 34. Piston 34 also has a threaded bore 70 for receiving screw 56. Screws 58 and 60 prevent actuator 54 from rotating with respect to the access of hollow barrel 12.

Screws 58 and 60 are also positioned along piston 34 to control the distance piston 34 moves with respect to slot 52, and consequently, the distance with which paddle 42 moves with respect to rigid tube 16. Alternatively, spacer 71 may ride in slot 52 to control the distance which actuator 54 and piston 34 move in slot 52. It can be seen from FIG. 2 that as actuator 54 moves back and forth along slot 52, paddle 42 will be retracted into or ejected from rigid tube 14.

Piston 34 may include recesses 100 and 102 about its distal and proximal ends to receive bushings 104 and 106 to facilitate easy sliding of piston 34 in barrel 12.

Figure 10:
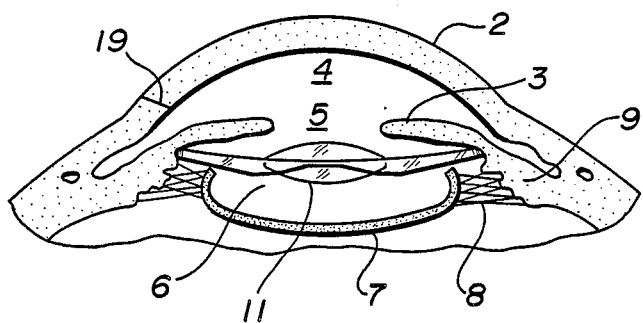
FIG. 10 shows a sectional schematic view of the anatomy of the eye with the lens in place.

Instrument 10 is used to insert an intraocular lens into the eye. A schematic illustration of a cross section through the eye is shown in FIG. 10. Corneal 2 is the front surface of the eye. Iris 3 divides the front portion of the eye into the anterior chamber 4 and the posterior chamber 6. Iris 3 is a sphincter which opens and closes in response to light and defines the pupil 5 through which light is transmitted to posterior chamber 6. The capsular bag 7 encapsulates the natural lens of the eye (not shown) and is preferably left in place after cataract extraction. Capsular bag 7 is supported by suspensory ligaments or zonulas 8 from cilliary muscle 9. Lens 11 is preferably placed in the posterior chamber. An incision 19 is shown in FIG. 10 through which lens 11 may be inserted into the eye using instrument 10 of the present invention. The operation of instrument 10 and the procedure for inserting lens 11 into the eye using instrument 10 will now be described.

Referring now to FIGS. 4 through 8, and particularly to FIG. 6, user removes intraocular lens 11 from its packages, picks it up with forceps (not shown) and places lens 11 in paddle 42 with the long axial dimension of the lens aligned generally with the axis of instrument 10. Lens 11 is cradled in paddle 42 so the user may inspect the lens prior to insertion. While holding the lens with forceps, the user may partially feed the lens into rigid tubular distal section 16 while retracting actuator 54 and correspondingly piston 34 and stylet 30 together into rigid tube 14. As lens 11 is retracted into rigid tube 14 the peripheral edges of holding portion 44 of paddle 42 wrap around and at least partially enfold lens 11.

Lens 11 is now ready for insertion into the eye using instrument 10. With lens 11 inside rigid tube 14, instrument 10 is rolled over to the position shown in FIGS. 1 and 2, 7 and 8 so that when lens 11 is ejected, paddle 42 will be positioned between cornea 2 and lens 11. Rigid tube 14 of instrument 10 is then inserted through incision 19 in cornea 2. The user may wish to position instrument 10 so that at least part of lens 11 may be placed behind iris 3 into posterior chamber 6.

The user then pushes actuator 54 distally along slot 52 in barrel 12 so as to push stylet 30 and piston 34 distally together and to move paddle 42 and lens 11 distally out of rigid tube 14 into the eye. The forward advance of actuator 54 in slot 52 is also controlled by the length of slot 52 and the position of screws 58 and 60 and spacer 71, if used. When screw 58 or spacer 71, if used, hits the distal end of slot 52 as shown in FIG. 2, the user knows that paddle 42 has advanced all the way into the eye so that lens 11 is in proper position.

The user must retract actuator 54 along slot 52 to retract paddle 42 within rigid portion 14 and then, after this retraction is accomplished, remove the entire instrument from the eye. The user may now position lens 11 in its proper place in the eye by manipulating lens 11 into the posterior chamber, preferably with the lens pressing against the ciliary muscle 9, by one of a variety of procedures which are irrelevant to the present invention and will not be described. It could be seen that instrument 10 provides an effective way of inserting intraocular lens 11 into the eye.

Air escape hole 21 in the proximal end of barrel 12 permits air to escape from the inside of hollow barrel as piston 34 retracts. Thus, compressed air does not inhibit the smooth motion of piston 34 in barrel 12.

Stylet 30 and paddle 42 can be disposable parts. The remaining parts can be reusable, sterilizable and durable materials which will become part of the surgeon's permanent instrument collection.

In the preferred embodiment, paddle 42 is disposable and used only for one patient. For the next patient, stylet 30 and paddle 42 are removed from the instrument by loosening screw 56. Paddle 42 is then removed from slot 40 at the distal end of stylet 30. Alternatively sleeve 41, if used, is slid off the distal end of stylet 30 and paddle 42 is removed. Stylet 30 and the other reusable parts of the instrument particularly rigid tube 14 which are exposed to ocular fluids, are then cleaned and sterilized and a new paddle 42 is installed. This is done by one of two methods. In one embodiment the margins 48 and 50 of paddle 42 are inserted in slot 40 of stylet 30 (FIGS. 11–13). In the other embodiment, mounting base 46 of paddle 42 is inserted in sleeve 41 and then both are press fit on the distal end of stylet 30 (FIGS. 2 and 3). Stylet 30 is then reinserted into piston 34 and screw 56 is tightened into position. The user will observe the alignment between holding portion 44 of paddle 42 with actuator 54 so that the surgeon will be conveniently able to confirm the orientation of the lens in the eye as it is ejected into position.

Alternatively, stylet 30 and paddle 42 are both made of disposable materials, assembled in the factory and sold as a sterile replacement part. In that embodiment the proximal end of stylet 30 is inserted in piston 34 and screw 56 is tightened into position. Before tightening screw 56 the surgeon will again check the alignment of holding portion 44 of paddle 42 as with the previous embodiment.

While the present invention has been described in connection with certain preferred embodiments, those skilled in the art will appreciate that certain modifications may be made without departing from the scope of the present invention. It is therefore, not intended that the present invention be limited except to set forth in the following claims.

I claim:

1. A lens holder for a surgical instrument used or inserting an intraocular lens into the eye comprising:
    an elongated stylet having a proximal end and a distal end and having an exterior surface;
    a flexible paddle;
    means for affixing said paddle to the distal end of said stylet so that said paddle extends distally from the distal end of said stylet including a slot extending transversely into said exterior surface of said stylet for receiving a portion of said paddle; and
    wherein the distal portion of said paddle includes a lens holding portion and the proximal portion of said paddle includes a mounting portion said mounting portion including margins to wrap around a distal portion of said stylet and fit into said slot.

2. The lens holder of claim 1 wherein said slot extends axially from the distal end of said stylet in a proximal direction.

3. The lens holder of claim 1 wherein said stylet distal portion includes a recess extending at least partially about said exterior surface of said stylet where said paddle is affixed to said stylet to provide a smooth transition from said paddle to said stylet exterior surface when said paddle is affixed to said stylet.

4. The lens holder of claim 1 further including means connected to said stylet for mounting said stylet within an instrument.

5. A surgical instrument for inserting an intraocular lens into the eye comprising:
    an elongated stylet having a proximal end and a distal end and having an exterior surface;
    a flexible paddle having a proximal and a distal portion;
    means for affixing said flexible paddle to the distal end of said stylet so that said paddle extends distally from said stylet;
    an axially extending generally annular tube having a distal end and a proximal end adapted to permit said stylet to reciprocate axially within said tube to permit said paddle to be retrated within said tube or to be ejected out of said tube;
    a generally annular hollow barrel;
    means cooperatively disposed on the distal end of said hollow barrel and the proximal end of said tube for connecting the two together;
    a slot extending through the side wall of said barrel;
    means for mounting said stylet for axial reciprocation within said barrel;

actuation means disposed along the outside surface of said barrel and at least partially projecting through said slot; and, means for operably connecting said actuation means to said stylet so that as said actuation means is moved with respect to said slot, said stylet will move with respect to said barrel to eject a lens into the eye.

6. The instrument of claim 5 further including an opening in a proximal portion of said barrel to allow air within said barrel to escape when said actuation means moves.

7. The instrument of claim 5 wherein said means for mounting said stylet within said barrel includes a generally cylindrical piston mounted for smooth reciprocation within said hollow barrel and operably connected to said actuation means; and, stop means associated with said actuation means to act in cooperation with said slot in the side wall of said barrel to control the distance which said stylet may reciprocate within said barrel.

8. The instrument of claim 7 further including bushings mounted on said piston to provide smooth motion of said piston within said barrel.

9. The instrument of claim 5 wherein said means for affixing said paddle to said stylet includes a slot extending transversely into said exterior surface of said stylet for receiving a portion of said paddle;

wherein the distal portion of said paddle includes a lens holding portion and the proximal portion of said paddle includes a mounting portion, said mounting portion including margins to wrap around a distal portion of said stylet and fit into said slot.

10. The instrument of claim 5 wherein said means for affixing said paddle to said stylet includes an annular sleeve;

wherein the distal portion of said paddle includes a lens holding portion and the proximal portion of said paddle includes a mounting portion, said mounting portion adapted to wrap around a distal portion of said stylet;

wherein said sleeve fits over a distal portion of said stylet and over the outside surface of said paddle mounting portion to hold said paddle in position.

11. A lens holder for a surgical instrument used or inserting an intraocular lens into the eye comprising:

an elongated stylet having a proximal end and a distal end and having an exterior surface;

a flexible paddle;

means for affixing said paddle to the distal end of said stylet so that said paddle extends distally from the distal end of said stylet including an annular sleeve adapted to fit about the distal end of said stylet;

wherein the distal portion of said paddle includes a lens holding portion and the proximal portion of said paddle includes a mounting portion wherein said mounting portion wraps around a distal portion of said stylet; and wherein said annular sleeve is adapted to fit tightly about the distal portion of said stylet and about the exterior surface of said mounting portion to provide a tight fit to hold said paddle in position.

12. The lens holder of claim 11 wherein said stylet distal portion includes a recess extending at least partially about said exterior surface of said stylet where said paddle is affixed to said stylet to provide a smooth transition from said paddle to said stylet exterior surface when said paddle is affixed to said stylet.

* * * * *